United States Patent
Pan et al.

(10) Patent No.: US 10,531,803 B2
(45) Date of Patent: Jan. 14, 2020

(54) INTRALIPID AS A CONTRAST AGENT TO ENHANCE SUBSURFACE BLOOD FLOW IMAGING

(71) Applicants: THE RESEARCH FOUNDATION FOR THE STATE UNIVERSITY OF NEW YORK, Albany, NY (US); THE UNITED STATES OF AMERICA, AS REPRESENTED BY THE SECRETARY, DEPARTMENT OF HEALTH AND HUMAN SERVICES, Bethesda, MD (US)

(72) Inventors: Yingtian Pan, East Setauket, NY (US); Congwu Du, East Setauket, NY (US); Hugang Ren, Irvine, CA (US); Nora Volkow, Bethesda, MD (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 31 days.

(21) Appl. No.: 14/414,183

(22) PCT Filed: Jul. 12, 2013

(86) PCT No.: PCT/US2013/050348
§ 371 (c)(1),
(2) Date: Jan. 12, 2015

(87) PCT Pub. No.: WO2014/012042
PCT Pub. Date: Jan. 16, 2014

(65) Prior Publication Data
US 2015/0209449 A1 Jul. 30, 2015

Related U.S. Application Data

(60) Provisional application No. 61/670,954, filed on Jul. 12, 2012.

(51) Int. Cl.
*A61B 5/026* (2006.01)
*A61B 5/0275* (2006.01)
*A61B 5/0285* (2006.01)
*A61B 5/00* (2006.01)
*A61K 49/00* (2006.01)

(52) U.S. Cl.
CPC ............ *A61B 5/0261* (2013.01); *A61B 5/004* (2013.01); *A61B 5/0275* (2013.01); *A61B 5/0285* (2013.01); *A61K 49/00* (2013.01); *A61K 49/0004* (2013.01); *A61B 5/0059* (2013.01)

(58) Field of Classification Search
None
See application file for complete search history.

(56) References Cited

U.S. PATENT DOCUMENTS

| 5,976,502 | A | * | 11/1999 | Khoobehi | A61K 49/0032 424/9.6 |
| 5,991,697 | A | * | 11/1999 | Nelson | G01P 5/26 356/28.5 |
| 6,245,018 | B1 | | 6/2001 | Lee | |
| 7,725,169 | B2 | * | 5/2010 | Boppart | A61B 5/0066 356/458 |
| 2001/0022963 | A1 | * | 9/2001 | Klaveness | A61K 49/001 424/9.6 |

FOREIGN PATENT DOCUMENTS

RU 2303400 7/2007

OTHER PUBLICATIONS

Rege et al. Imaging microvascular flow characteristics using laser speckle contrast imaging. 2010 Conf. Proc. IEEE Eng. Med. Biol. Soc. 2010: 1978-1981.*
Jain et al. Angiogenesis in brain tumours. 2007 Nat. Rev. Neurosci. 8: 610-622.*
Production information for INTRALIPID. 9 pages. <medsafe.govt.nz/profs/datasheet/i/Intralipidinf.pdf>. Accessed May 30, 2017.*
Van Staveren et al. Light scattering in Intralipid-10% in the wavelength range of 400-1100 nm. 1991 Appl. Opt. 30: 4507-4514. (Year: 1991).*
Lee et al. Engineered microsphere contrast agents for optical coherence tomography. 2003 Opt. Lett. 28: 1546-1548. (Year: 2003).*
Chen et al. Noninvasive imaging of in vivo blood flow velocity using optical Doppler tomography. 1997 Opt. Lett. 22: 1119-1121. Year: 1997).*
International Search Report for International Patent Application No. PCT/US2013/050348 dated Oct. 31, 2013.
International Written Opinion for International Patent Application No. PCT/US2013/050348 dated Oct. 31, 2013.
Mehmet Kaya, et al. "Acoustic Responses of Monodisperse Lipid-Encapsulated Microbubble Contrast Agents Produced by Flow Focusing," Bubble Sci Eg. Tech., 2(2):33-40 (Dec. 2010).
Jason R. Cook et al. "Tissue-Mimicking Phantoms for Photoacoustic and Ultrasonic Imaging," Bio Optics Express, vol. 2, No. 11, pp. 3193-3206 (Nov. 1, 2011).
Yimin Wang et al. "Pilot Study of Optical Coherence Tomography Measurement of Retinal . . . ," Investigative Ophthalmology & Visual Science vol. 52, No. 2, pp. 840-845 Feb. 2011.
Novik M. B. et al. "Lokalnaya Tserebrovaskulyarnaya Reaktivnost u bolnykh s glialnyumi . . . ." Neirokhirurgiya, No. 3, pp. 27-33 (2011).

(Continued)

*Primary Examiner* — Jennifer A. Lamberski
(74) *Attorney, Agent, or Firm* — Hunton Andrews Kurth LLP

(57) ABSTRACT

The present invention provides a method of imaging blood vessels or blood flow in blood vessels in an animal comprising:
(i) injecting a lipid solution into the bloodstream of the animal;
(ii) imaging the blood vessels by an imaging method; and
(iii) calculating the blood flow velocity in the blood vessels.

25 Claims, 7 Drawing Sheets

(56) References Cited

OTHER PUBLICATIONS

Chen, Z. et al. (1998) Optical Doppler Tomography: Imaging in vivo Blood . . . Pharmacological Intervention & Photodynamic Therapy, Photochemistry and Photobiology, vol. 67, 1-7.

Chen, Z. et al. (1999) Optical Doppler Tomography, IEEE Journal of Selected Topics in Quantum Electronics, vol. 5, No. 4, 1134-1142.

Draijer, M. et al. (2009) Review of laser speckle contrast techniques for visualizing tissue pattern, Lasers Med Sci, 24, 639-651.

Dunn, A. K. (2012) Laser speckle contrast imaging of cerebral blood flow, Annals of Biomedical Engineering, vol. 20, No. 2, 367-377.

Hugang Ren, et al. (2012) Quantitative imaging of red blood cell velocity invivo using optical coherence Doppler tomography. Appl. Phys. Lett. 100, 233702.

Hugang Ren, et al. (2012) Cerebral blood flow imaged with ultrahigh-resolution optical coherence angiography and Doppler tomography. Optics Letters, 37 (8), 1388-1390.

Manavi, M.V. (2010) Lipid Infusion as a treatment for local anesthetic toxicity: a literature review. AANA J. 78, 1, 69-78.

Mirallo, J.M. et al. (2010) State of the art review: Intravenous fat emulsions: Current applications, safety profile, & clinical implications. Ann Pharmacother. 44, 4, 688-700.

Ren, H., et al. (2012) Cocaine-induced cortical microischemia in the rodent brain: clinical implications, Molecular Psychiatry, 10, 1017-1025.

Rosenblatt M.A. et al (2006) Successful Use of a 20% Lipid Emulsion to Resuscitate a Patient after a Presumed Bupi vacaine-related Cardiac Arrest. Anesthesiology, 105, 217-218.

Vakoc, B.J. et al. (2009) Three-dimensional microscopy of the tumor microenvironment in vivo using optical frequency domain imaging, Nature Medicine, vol. 15 (10), 1219-1223.

Wang RK, et al. (2007) Three dimensional optical angiography. Optics Express, vol. 15, No. 7, 4083-4097.

Yuan Z. et al. (2011) Imaging separation of neuronal from vascular effects of cocaine on rat cortical brain in vivo. vol. 54, No. 2, 1130-1139.

* cited by examiner

INTRALIPID AS A CONTRAST AGENT TO ENHANCE SUBSURFACE BLOOD FLOW IMAGING

CROSS REFERENCE TO RELATED APPLICATION(S)

This present application is based upon and claims the benefit under 35 U.S.C. § 119(e) of priority from International Application No. PCT/US2013/050348 filed on Jul. 12, 2013, which claims the benefit of priority from U.S. Provisional Application Ser. No. 61/670,954 filed on Jul. 12, 2012, the contents of the entire disclosures of which are incorporated herein by reference.

The invention was made with government support under Grant numbers DA029718, DA028534, and DA032228 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Laser Doppler flowmetry (LDF) is the technique of using the Doppler shift in a laser beam to determine the velocity of translucent or semi-transparent fluid flow. Laser light that is reflected fluctuates in intensity, the frequency of which is equivalent to the Doppler shift between the incident and scattered light. The Doppler frequency shift is proportional to the component of particle velocity. LDF is based on detection of Doppler frequency shift induced by moving particles, for example, red blood cells, with respect to the direction of the incident light, i.e., $f_D = 2\pi/\lambda \cdot v \cos \theta$ where $v$ is the velocity of moving particles (backscatterers) and $\theta$ is the incline angle.

LDF is a noninvasive method for measuring the continuous circulation of blood flow on a microscopic level. Currently LDF is used in dermatology, facial surgery, vascular surgery, dental applications, ocular applications, transplant surgeries, cardiac surgery, pharmacology, and exercise physiology. Detection of blood flow abnormalities is crucial in these areas of medicine.

Optical coherence tomography (OCT) is an optical signal acquisition and processing method capable of capturing 3D images from within optical scattering media with µm resolution. OCT uses an optical beam that is directed at the tissue. A portion of the light reflects but most scatters off at large angles. The diffusely scattered light contributes background that obscures the image. OCT uses optical coherence to record the optical path length of received photons allowing rejection of most photons that scatter multiple times before detection. Therefore, OCT allows for clear 3D images by rejecting background noises or artifacts while collecting light directly reflected from surfaces of interest.

Optical coherence Doppler tomography (ODT) operates by combining the merits of OCT and LDF to provide high-resolution 3D Doppler blood flow imaging with a superior spatial resolution, for example, 2-10 µm. ODT is an optical technique for imaging both the tissue structure and the flow velocity of moving particles in highly scattering media. ODT is also noninvasive. The high spatial resolution of ODT allows for many potential applications in the clinical management of patients in whom imaging tissue structure and monitoring blood flow dynamics are essential (Chen et al. 1998; Chen et al. 1999).

ODT to detect minute microcirculation, which is critical to a number of clinical diagnoses (e.g., early detection of neo-angiogenesis after wound healing, detection of tumor microenvironment, retinal blood flow imaging, functional brain imaging, neuronal rehabilitation), remains a technical challenge, especially for quantitative imaging of capillary blood flow as is needed for functional brain imaging.

SUMMARY OF THE INVENTION

The present invention provides a method of imaging blood vessels or blood flow in blood vessels in an animal comprising:
  (i) injecting a lipid solution into the bloodstream of the animal;
  (ii) imaging the blood vessels by an imaging method; and
  (iii) calculating the blood flow velocity in the blood vessels.

The present invention provides a method of distinguishing between different types of animal microvasculature comprising:
  (i) injecting a lipid solution into the bloodstream of the animal;
  (ii) imaging the blood vessels by an imaging method; and
  (iii) calculating the blood flow velocity in the blood vessels.

The present invention provides a Optical Doppler Tomography (ODT) method of imaging blood vessels or blood flow in blood vessels in an animal comprising:
  (i) injecting a lipid solution into the bloodstream of the animal so that the blood stream carries the intralipid to a specific site;
  (ii) applying a laser beam to the specific site so as to generate a Doppler frequency shift of the laser caused by the intralipid flowing through the blood vessels at the specific site; and
  (iii) generating a three-dimensional tomographic image of the blood vessels at the specific site on the basis of the Doppler frequency shift of the laser; and
  (iv) calculating the blood flow velocity in the blood vessels at the specific site on the basis of the Doppler frequency shift of the laser.

DETAILED DESCRIPTION OF THE INVENTION

Figure 1:
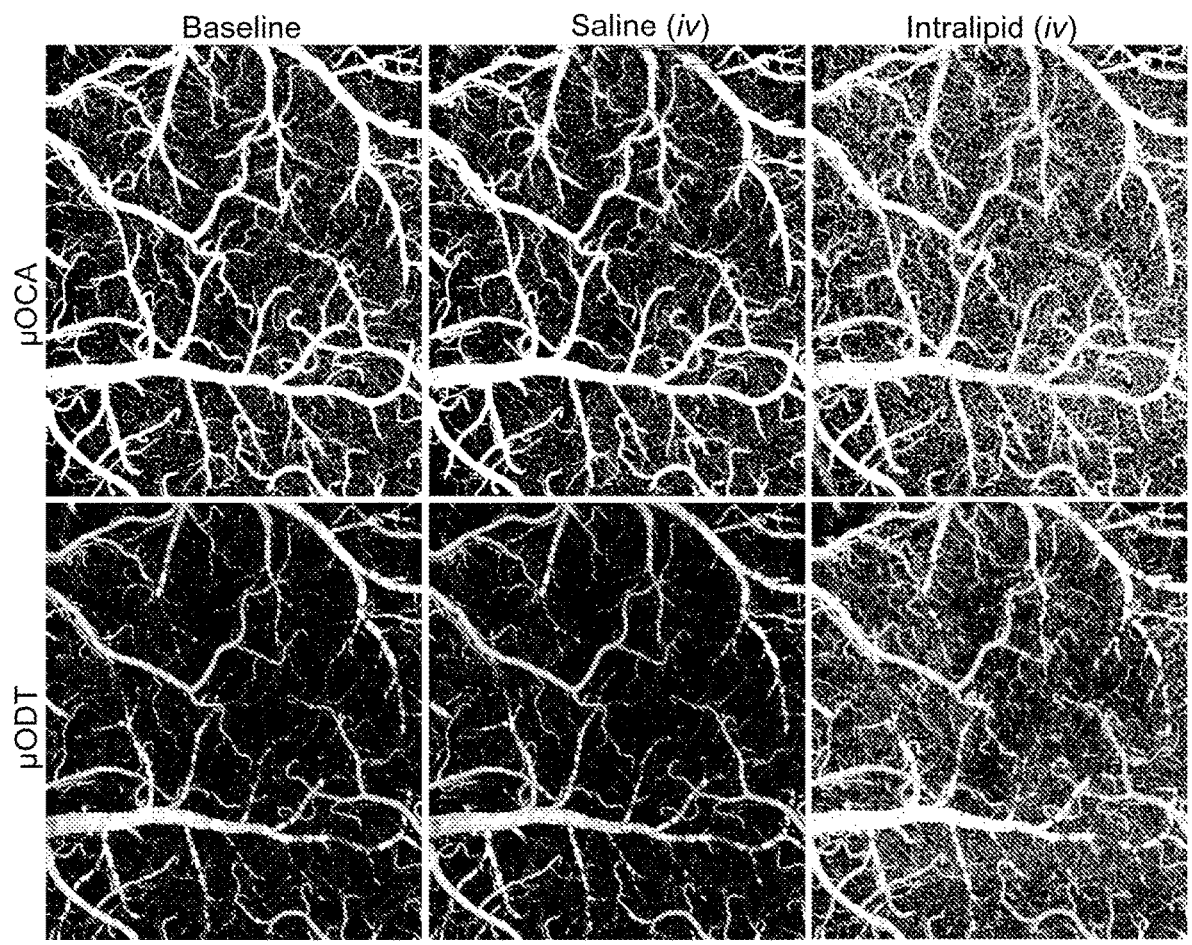
FIG. 1. Ultrahigh-resolution optical coherence angiography (µOCA) and ultrahigh-resolution optical coherence Doppler tomography (µODT) images (upper and lower panels) of mouse cortical cerebrovascular network during baseline; after injections of ~0.15 mL saline and intralipid 20 intravenously.

The present invention provides a method of imaging blood vessels in an animal comprising:

(i) injecting an intralipid into the bloodstream of the animal;
(ii) imaging the blood vessels by an imaging method; and
(iii) calculating the blood flow velocity in the blood vessels.

In some embodiments of the method, further comprising
(iv) quantitatively determining the blood flow velocity change following intralipid injection.

The present invention provides a method of distinguishing between different types of animal microvasculature comprising:

(i) injecting an intralipid into the bloodstream of the animal;
(ii) imaging the blood vessels by an imaging method; and
(iii) calculating the blood flow velocity in the blood vessels.

In some embodiments of the method, wherein the imaging method is Optical Doppler Tomography (ODT).

In some embodiments of the method, wherein the imaging method is Laser Speckle Contrast Imaging (LSCI).

In some embodiments of the method, wherein the intralipid is a contrast agent.

In some embodiments of the method, wherein the blood vessel imaging of the animal is enhanced relative to an animal that was not injected with the intralipid.

In some embodiments of the method, wherein a three-dimensional image of the blood vessels is generated.

In some embodiments of the method, wherein the intralipid is intralipid 10%, intralipid 20%, or intralipid 30%.

In some embodiments of the method, wherein the blood vessel is a capillary.

In some embodiments of the method, wherein the blood flow in the capillary is impossible to image or the blood flow velocity of the blood flow in the capillary is impossible to measure without the intralipid contrast agent.

In some embodiments of the method, wherein the animal is a mammal.

In some embodiments of the method, wherein the mammal is a human.

In some embodiments of the method, wherein a tumor microvasculature is distinguished from a non-tumor microvasculature.

In some embodiments of the method, wherein a cancer microvasculature is distinguished from a non-cancer microvasculature.

In some embodiments of the method, wherein the tumor is a glioblastoma multiforme.

The present invention provides Optical Doppler Tomography (ODT) method of imaging blood vessels in an animal comprising:

(i) injecting an intralipid into the bloodstream of the animal so that the blood stream carries the intralipid to a specific site;
(ii) applying a laser beam to the specific site so as to generate a Doppler frequency shift of the laser caused by the intralipid flowing through the blood vessels at the specific site; and
(iii) generating a three-dimensional tomographic image of the blood vessels at the specific site on the basis of the Doppler frequency shift of the laser; and
(iv) calculating the blood flow velocity in the blood vessels at the specific site on the basis of the Doppler frequency shift of the laser.

The present invention provides a method of imaging blood vessels or blood flow in blood vessels in an animal comprising:

(i) injecting a lipid solution into the bloodstream of the animal;
(ii) imaging the blood vessels by an imaging method; and
(iii) calculating the blood flow velocity in the blood vessels.

In some embodiments of the above method, comprising:
(i) injecting an intralipid into the bloodstream of the animal;
(ii) imaging the blood vessels by an imaging method; and
(iii) calculating the blood flow velocity in the blood vessels.

In some embodiments of the method, further comprising
(iv) quantitatively determining the blood flow velocity change following intralipid injection.

The present invention provides a method of distinguishing between different types of animal microvasculature comprising:
(i) injecting a lipid solution into the bloodstream of the animal;
(ii) imaging the blood vessels by an imaging method; and
(iii) calculating the blood flow velocity in the blood vessels.

In some embodiments of the above method, comprising:
(i) injecting an intralipid into the bloodstream of the animal;
(ii) imaging the blood vessels by an imaging method; and
(iii) calculating the blood flow velocity in the blood vessels.

In some embodiments of the method, wherein the imaging method is Optical Doppler Tomography (ODT).

In some embodiments of the method, wherein the imaging method is Laser Speckle Contrast Imaging (LSCI).

In some embodiments of the method, wherein the lipid solution is a contrast agent.

In some embodiments of the method, wherein the intralipid is a contrast agent.

In some embodiments of the method, wherein the blood vessel imaging of the animal is enhanced relative to an animal that was not injected with the lipid solution.

In some embodiments of the method, wherein the blood vessel imaging of the animal is enhanced relative to an animal that was not injected with the intralipid.

In some embodiments of the method, wherein a three-dimensional image of the blood vessels is generated.

In some embodiments of the method, wherein the intralipid is intralipid 10%, intralipid 20%, or intralipid 30%.

In some embodiments of the method, wherein the blood vessels are capillaries.

In some embodiments of the method, wherein the blood flow in the capillaries is impossible to image or the blood flow velocity of the blood flow in the capillaries is impossible to calculate, without the lipid solution.

In some embodiments of the method, wherein the animal is a mammal. In some embodiments of the method, wherein the mammal is a human.

In some embodiments of the method, wherein a tumor microvasculature is distinguished from a non-tumor microvasculature. In some embodiments of the method, wherein the tumor is a glioblastoma multiforme.

The present invention provides a Optical Doppler Tomography (ODT) method of imaging blood vessels or blood flow in blood vessels in an animal comprising:
(i) injecting a lipid solution into the bloodstream of the animal so that the blood stream carries the intralipid to a specific site;
(ii) applying a laser beam to the specific site so as to generate a Doppler frequency shift of the laser caused by the intralipid flowing through the blood vessels at the specific site; and
(iii) generating a three-dimensional tomographic image of the blood vessels at the specific site on the basis of the Doppler frequency shift of the laser; and
(iv) calculating the blood flow velocity in the blood vessels at the specific site on the basis of the Doppler frequency shift of the laser.

In some embodiments of the above method, comprising:
(i) injecting an intralipid into the bloodstream of the animal so that the blood stream carries the intralipid to a specific site;
(ii) applying a laser beam to the specific site so as to generate a Doppler frequency shift of the laser caused by the intralipid flowing through the blood vessels at the specific site; and
(iii) generating a three-dimensional tomographic image of the blood vessels at the specific site on the basis of the Doppler frequency shift of the laser; and
(iv) calculating the blood flow velocity in the blood vessels at the specific site on the basis of the Doppler frequency shift of the laser.

In some embodiments of the method, wherein the blood vessels are capillaries.

In some embodiments of the method, wherein the blood flow imaging is enhanced relative to ultrahigh-resolution optical coherence angiography (µOCA) methods.

In some embodiments of the method, wherein the blood vessels or the blood flow in the blood vessels are imaged one or more times following injection of the intralipid. In some embodiments of the method, wherein the blood vessels or the blood flow in the blood vessels are imaged two or more times following injection of the intralipid. In some embodiments of the method, wherein the blood vessels or the blood flow in the blood vessels are imaged three or more times following injection of the intralipid.

In some embodiments of the method, wherein the blood vessels or the blood flow in the blood vessels are imaged within 1 hour following injection of the intralipid. In some embodiments of the method, wherein the blood vessels or the blood flow in the blood vessels are imaged within 3 hours following injection of the intralipid. In some embodiments of the method, wherein the blood vessels or the blood flow in the blood vessels are imaged within 6 hour following injection of the intralipid.

As used herein, "Optical coherence Doppler tomography" is a technique that combines laser Doppler flowmetry (LDF) with optical coherence tomography (OCT) to obtain high-resolution tomographic velocity and structural images of static and moving constituents in highly scattering biological tissues. "Optical coherence Doppler tomography" is also referred to herein as "ODT" or "Optical Doppler tomography".

As used herein, "Laser Speckle Imaging (LSI)" or "Laser Speckle Contrast Imaging (LSCI)" is a non-invasive blood flow imaging technique that can provide information on the state of biological tissues and the efficiency of disease treatment. The technique focuses on interpreting the speckle pattern phenomenon that occurs when electromagnetic light waves interfere with one another to produce optically visible effects in both the spatial and temporal regions of the remitted reflectance pattern. Analysis of these speckle patterns can result in quantitative wide-field imaging data pertaining to blood flow velocity mapping. See Draijer, M. et al. (2009) and Dunn, A. K. (2012).

As used herein, "lipid solution" is any solution comprising lipids or microlipids. Lipid solutions include, but are not limited to, intralipid, total parenteral nutrition (TPN) solution, parental nutrition (PN) solution or total peripheral nutrition (TPN) solution. The solution may be customized or standardized solutions may be used. In some embodiments, the lipid solution is white.

As used herein, "intralipid" is a fat emulsion that is used clinically as an intravenously administered nutrient. It is available in 10%, 20% and 30% concentrations. It is comprised of soybean oil, egg yolk phospholipids, glycerin, and water. The major fatty acid components of intralipid are linoleic acid, oleic acid, palmitic acid, linolenic acid and stearic acid. Intralipids have been used in various applications as are described in Mirtallo, J. M. et al. 2010 and Manavi, M. V. 2010, the contents of each of which are hereby incorporated by reference. Intralipids are effective to save patients who were unresponsive to standard resuscitation methods following severe cardiotoxicity secondary to intravenous overdose of local anesthetic drugs (Rosenblatt, M. A. et al. 2006).

The intralipid used in the method of the present invention may be purchased from a variety of chemical suppliers including Sigma-Aldrich, St. Louis, Mo., USA (Intralipid 20%: Catalog No. 1141) or Baxter, Deerfield, Ill., USA (Intralipid 20%: product code 2B6023, Intralipid 30%: product code 2B6053). However, this may not be the only means by which to obtain the desired intralipid. Other commercially available total parenteral nutrition (TPN) can also be used.

Total parenteral nutrition (TPN) solution, parental nutrition (PN) solution and total peripheral nutrition (TPN) solution are within the scope of this invention.

In any one of the above embodiments, a total parenteral nutrition (TPN) solution, parental nutrition (PN) solution or total peripheral nutrition (TPN) solution is used.

The TPN, PN and TPN solutions may be customized to individual patient requirements, or standardized solutions may be used. The solutions may contain water, amino acids, vitamins, minerals, carbohydrates, electrolytes and/or lipids. In one embodiment, the solutions contain high scattering lipids or microlipids.

As used herein, "contrast agent" is a substance used to enhance the visibility of internal bodily structures in medical imaging. Contrast agents are commonly used to enhance the visibility of blood vessels.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Material and Methods

The detailed methods of ultrahigh-resolution OCT, animal preparation, and in vivo blood flow imaging in mouse brain has been previously outlined in Ren, H. et al. 2012, the contents of which are hereby incorporated by reference.

Surgery: Mice were anesthetized with inhalational 2% isoflurane (in 100% $O_2$) and mounted on a custom stereotaxic frame to minimize motion artifacts. A ~$\phi$5 mm cranial window was created above the right somatosensory motor cortex. The exposed cortical surface was immediately covered with 2% agarose gel and affixed with a 100 μm-thick glass coverslip using biocompatible cyanocrylic glue. The physiological state of the mice was continuously monitored (SA Instruments, NY).

Intravenous intralipid/saline induction: A mouse tail vein was cannulated with a 30-gauge hypodermic needle connected to PE10 tubing, through which a bolus of intralipid or saline (~0.15 ml) was administered (<15 sec).

In vivo imaging: A custom ultrahigh-resolution optical coherence tomography (μOCT) system developed in our lab was used to acquire 3D cross-sectional images of cortical brain structures characterized by their backscattering properties at near real time and over a large field of view (e.g., 2×2×1 mm$^3$) through the cranial window, and post-image processing was applied to render μOCA and quantitative μODT images of the cerebral microvascular networks in vivo. The axial resolution of μOCA/μODT is 1.8 μm, as determined by the coherence length $(L_c=2(\ln2)^{1/2}/\pi \cdot \lambda^2/\Delta\lambda_{cp})$ of a 8 fs Ti: Sapphire laser system used (λ=800 nm; $\Delta\lambda_{cp}$≈154 nm, cross-spectrum); its transverse resolution is 3 μm, as determined by the focal spot size of the microscopic objective employed (f16 mm/NA0.25). High-density B-scans (e.g., 16 k sequential A-scans along the immediate transverse scanning axis, e.g., x-axis) were performed to enhance the detection of minute Doppler frequency shift of capillary flows. The technical details of μOCA/μODT are provided in Supplementary Information of Ren, H. et al., Molecular Psychiatry, 2012. 3D flow data are presented by maximum intensity projection (MIP) or other 3D volume-rendering image platforms, as shown in the figures below with μOCA and μOCM presented in gray-scale and pseudo-color (color transition reflects the flow rate difference).

Example 1. Cerebral Blood Flow

An ODT method was used to image the microcirculatory network of a mouse cortex (FIG. 1). The experiment compared the ODT imaging of a mouse injected with ~0.15 mL saline, a mouse injected with ~0.15 mL intralipid 20%, and a control. The ODT image of the mouse cortical cerebro-vascular network was clearly enhanced as a result of the intravenous injection of intralipid 20%. The blood flow velocity is also obtained using the ODT imaging method. Importantly, the major improvement is on the capillary networks, which were barely seen without the injection of the intralipid.

In the experiment, a cranial window was created surgically and the image size was 1 mm (wide) by 1.2 mm (high) by 1 mm (deep) on a mouse cortex. Injection of saline or intralipid was through a tail vein with the amount of ~0.15 mL/each OCA/ODT imaging was performed 5 min after the injection. Detailed experimental procedures are described in Ren et al. Molecular Psychiatry 2012, the contents of which are hereby incorporated by reference.

Figure 2:
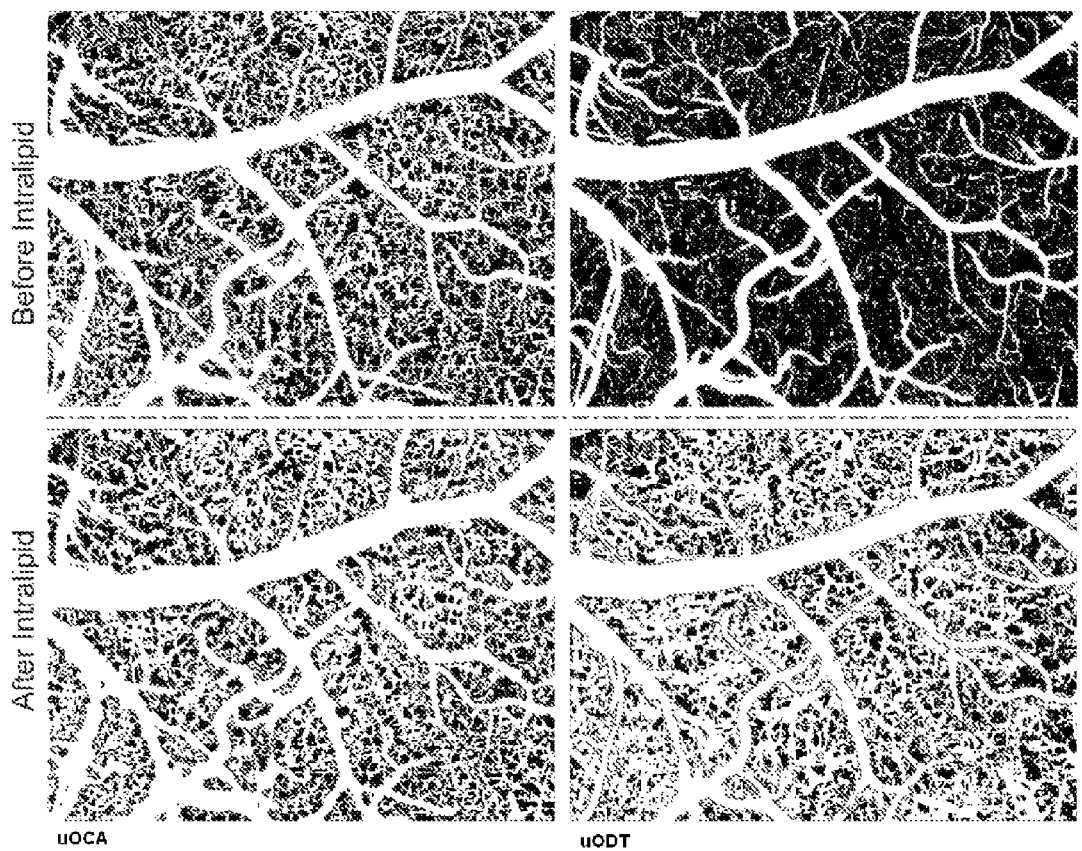
FIG. 2. Analysis of microvascular fill factor following injection before and after intralipid injection. Segmented regions in larger vessels as well as the CBFs within these vessels are excluded to analyze minute capillaries and capillary flows. Fill factor is defined as the percentage of pixels taken by capillaries vs those of the entire pixels. The bar chart shows that the major improvement of this approach is on quantitative imaging of capillary flow (µODT), e.g. with fill factor from ~17% to ~58% although that of micro vasculature (µOCA) also increased from ~53% to ~58%. More importantly, after intralipid injection, the fill factor detected by µODT (~58%) approached (p=0.4) that detected by µOCA (~62%), suggesting that this method allowed to enhance the sensitivity of capillary flow imaging to the angiography-limited detection sensitivity.
Figure 2:
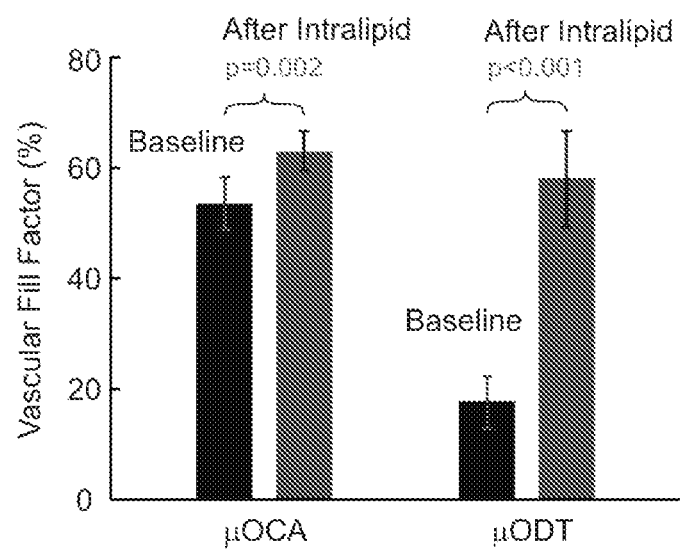

Example 2. Minimal Detectable Capillary Cerebral Blood Flows by Intralipid Injection Quantitative analysis of FIG. 2 (similar to FIG. 1 except images are binarized) shows that the fill factor (all pixels with detectable flows divided by the total pixels) of the capillaries (regions within major vessels are excluded) are enhanced significantly from 17% to 58% for μODT; That of μOCA was also increased from 53% to 62% (Right panel in FIG. 2). More importantly, although the fill factor of μODT after intralipid was still lower than that of μOCA, the difference is not significant (p=0.4), suggesting that with intralipid, the sensitivity of μODT was dramatically improved to be comparable to μOCA.

Figure 3:
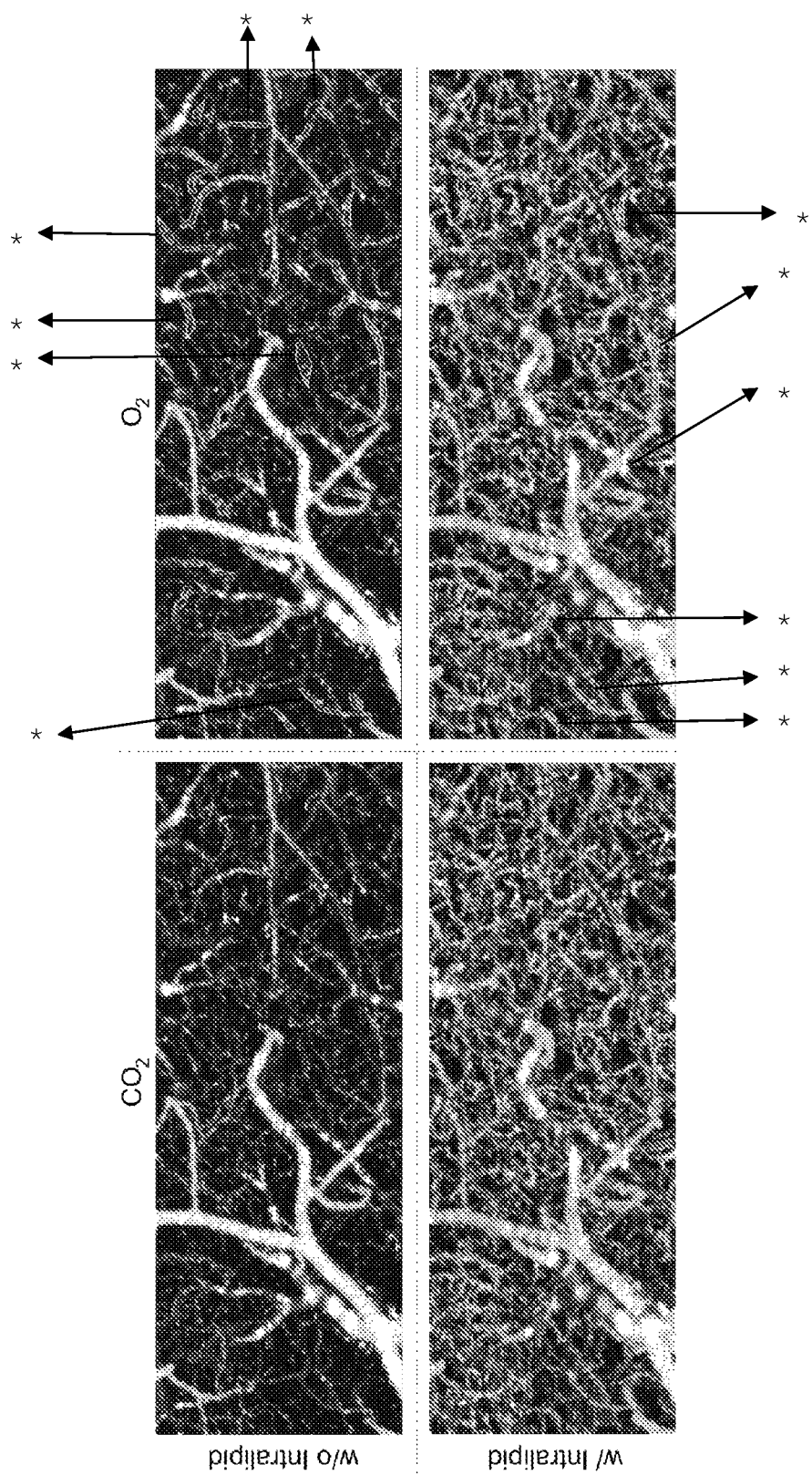
FIG. 3. μODT images of blood flow change in response to physiological/functional change of the brain, e.g., from mild hypercapnia to normocapnia. The results based on capillary flow rates measured within 5 regions of interest (asterisks indicated by arrow indicate selected regions of interest) show that with injection of intralipid, increase of detectable flows enhanced 0.313/0.0323=9.7 folds for normocapnia and 0.368/0.0473=7.8 folds for mild hypercapnia. In the calculation, a SNR>1.5 (over the background—no flow pixels) was used to segment flows.

Example 3. Cerebral Blood Flow in Response to Physiological/Functional Changes from Mild Hypercapnia to Normocapnia FIG. 3 shows an example of enhancing the detection of the cerebral blood flow change in response to physiological/functional change of the brain, e.g., from hypercapnia to normocapnia. Experiments were performed after a mouse was anesthetized under 2% isofluorine with pure $O_2$. Before the imaging, $O_2$ gas was switched to 95% $O_2$ with 5% $CO_2$ to induce mild hypercapnia. OCA/ODT imaging was performed. Then, it was switched back to 100% $O_2$ followed by a 10 min waiting period to allow for stabilization of the physiological condition to perform the 2nd group of imaging experiments.

After the baseline study was done, gas was switched back 95% $O_2$ with 5% $CO_2$ and iv injection of ~0.15 mL intralipid-20 was delivered follow by a 10 min delay before scanning. The same two sets of imaging studies were performed as done for the baseline studies prior to intralipid injection. To minimize the drift in the animal's physiologic conditions (decline of blood flow with time for anaesthetized rodents), a small image size (1.2 mm by 0.5 mm of a cortical surface) was chosen to facilitate fast image acquisition.

Figure 4:
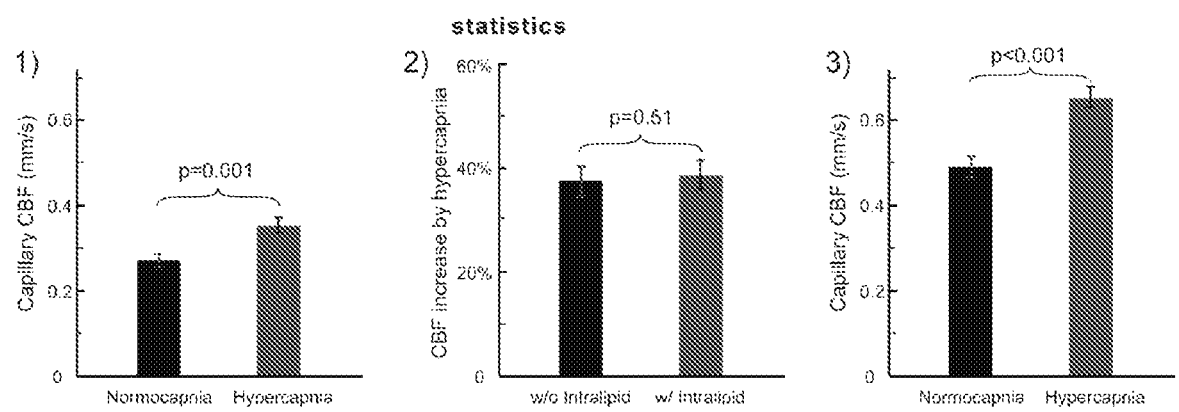
FIG. 4. Quantitative analysis of capillary flow changes between mormocapnia and mild hypercapnia in FIG. 3. 1) Mean capillary CBF increase in baseline period; 3) Mean capillary CBF increase after intralipid injection. 2). The increase rate is almost identical (~37% vs 38%, p=0.51). This result suggests that not only intralipid significantly enhance the sensitivity for capillary flow detection, it also maintains the nature for quantitative detection of CBF changes, which is critical to various brain physiological/pharmacological/functional studies.

For post image processing and analysis, about 20 spots (see circled small regions in FIG. 3 in the capillary networks were randomly selected to compare flow velocity changes induced when shifting from hypercapnia to normocapnia and the same fields of view were used to compare before and after injection of intralipid. The average flow change and standard deviation indicated that intralipid injection substantially increased the absolute flow rates—critical to detecting capillary flows. The blood flow rates were monitored (FIG. 4), their increases from normocapnia to hypercapnia were quantified, i.e., from 0.27 mm/s to 0.35 mm/s (FIG. 4-1) in baseline and from 0.48 mm/s to 0.63 mm/s after intralipid injection. Importantly, their increase rates were 37% and 38% (FIG. 4-2), showing a good correlation. This result shows that with intralipid injection, the sensitivity for detection of capillary flow is significantly enhanced and more importantly it maintains the ability to detect quantitative flow change, which is suitable for studying various brain physiological, functional and pharmacological changes.

Example 4. Additional Imaging Targets

The ODT method described herein is also used in brain imaging, pharmacological imaging of brain physiology and function, imaging of the cancer microenvironment (tumor angiogenesis) and imaging of wound healing.

Figure 5:
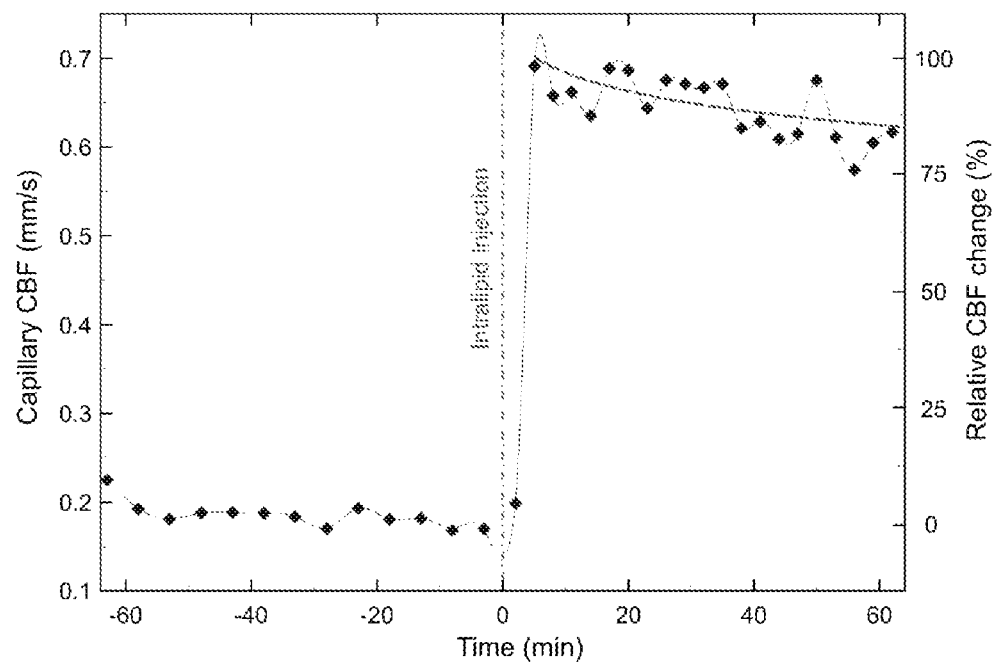
FIG. 5. Clearance characteristics of intralipid (iv) for capillary CBF imaging. The measurement data (diamonds) are the average CBF rates from randomly selected 10 regions of interest (i.e., within capillaries). The result shows that the clearance effects after intralipid injection was slow (i.e., decreased 14% in 60 min), suggesting that this method can be used for various time-lapse imaging studies (e.g., study pharmacological effects).

FIG. 5 shows the intralipid clearance curve. This result shows that over a long period time after intralipid injection, i.e., 1 hour, flow decrease due to intralipid clearance was from 100% to 86%, i.e., less than 14%. Given the long duration, time-lapse brain imaging studies, such as that in FIG. 2 and cocaine-induced blood flow change, and many other pharmacological activation as well as optogenetic activations, are studied by this approach.

Example 5. Measuring Blood Flow Velocity (Red Blood Cell Velocity in a Capillary)

The ODT method described herein is also used to measure blood flow velocity. Computation of blood flow velocity is based on know methods (Wang et al. 2007). Traditionally, such measurement has been done by calculating the phase difference between adjacent A-scans (i.e., Phase subtraction method or PSM). Other methods include 1) digital-frequency-ramping OCT or DFR-OCT, 2) phase-intensity-mapping or PIM method published from our lab (Yuan et al. 2011). These methods are based on either FFT or Hilbert transform in the lateral direction to enhance the SNR or minimize phase noise due to tissue heterogeneity and motion artifacts to the phase detection.

Figure 6:
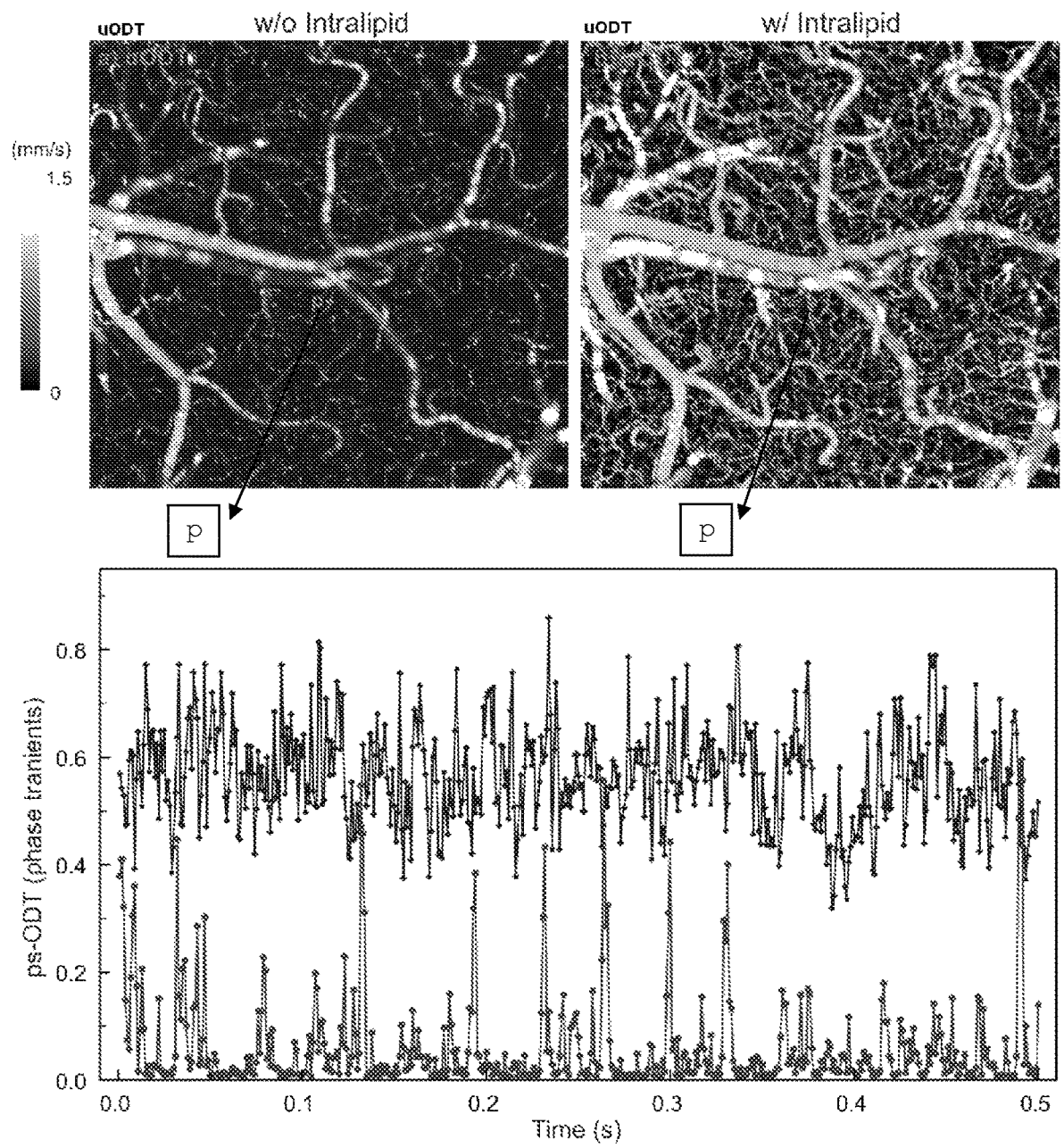
FIG. 6. Comparison of capillary CBF between baseline and after intralipid injection as measured by ps-uODT. a) and b): uODT of mouse CBF images without and with intralipid injection, respectively. p: a capillary chosen for ps-uODT to measure capillary RBC velocity. The lower panel shows time traces of ps-uODT without intralipid (lower trace) and after intralipid injection (upper trace). The spikes in red trace (each spike corresponds to a phase transition induced by red blood cell passing through the scanning cross section p) disappear; instead, they are elevated to be largely continuous due to high numbers of micro lipid particles in the blood stream that continuously contribute to the detected Doppler signal or phase transients. This explains the working principle of this method: the high latency between 2 flowing RBCs that causes underestimated RBC velocity is overcame by the abundant intralipid microlipids (strong backscatterers) which presumably flowing at nearly the same speed with adjacent RBCs.

FIG. 6 shows, by tracking a capillary P using particle-counting μODT (PS-μODT, Ren et al. Appl. Phys. Lett. 2012), the time traces indicate that without intrapid, the spikes in the lower trace, where the counts of discrete red blood cells passing through discretely with large idle time gaps, underestimate flow. Whereas with intralipid, the higher curves show that the gaps were filled with intalipid particles and became continuous, thereby eliminating the underestimation of capillary flows due to long latency artifacts.

Example 6. Tumor Microvasculature

The ODT method described herein is also used to distinguish between different types of animal microvasculature. Current brain imaging modalities are unable to distinguish between true tumor progression and psudoprogression in the case of GBM (Glioblastoma Multiforme) after concurrent treatments of drug and radiation. However, the microvasculature is quite different between the two (Vakoc et al. 2009). The method described herein highlights capillaries and capillary blood flow and is capable of scanning a large tumor within seconds or minutes.

Figure 7:
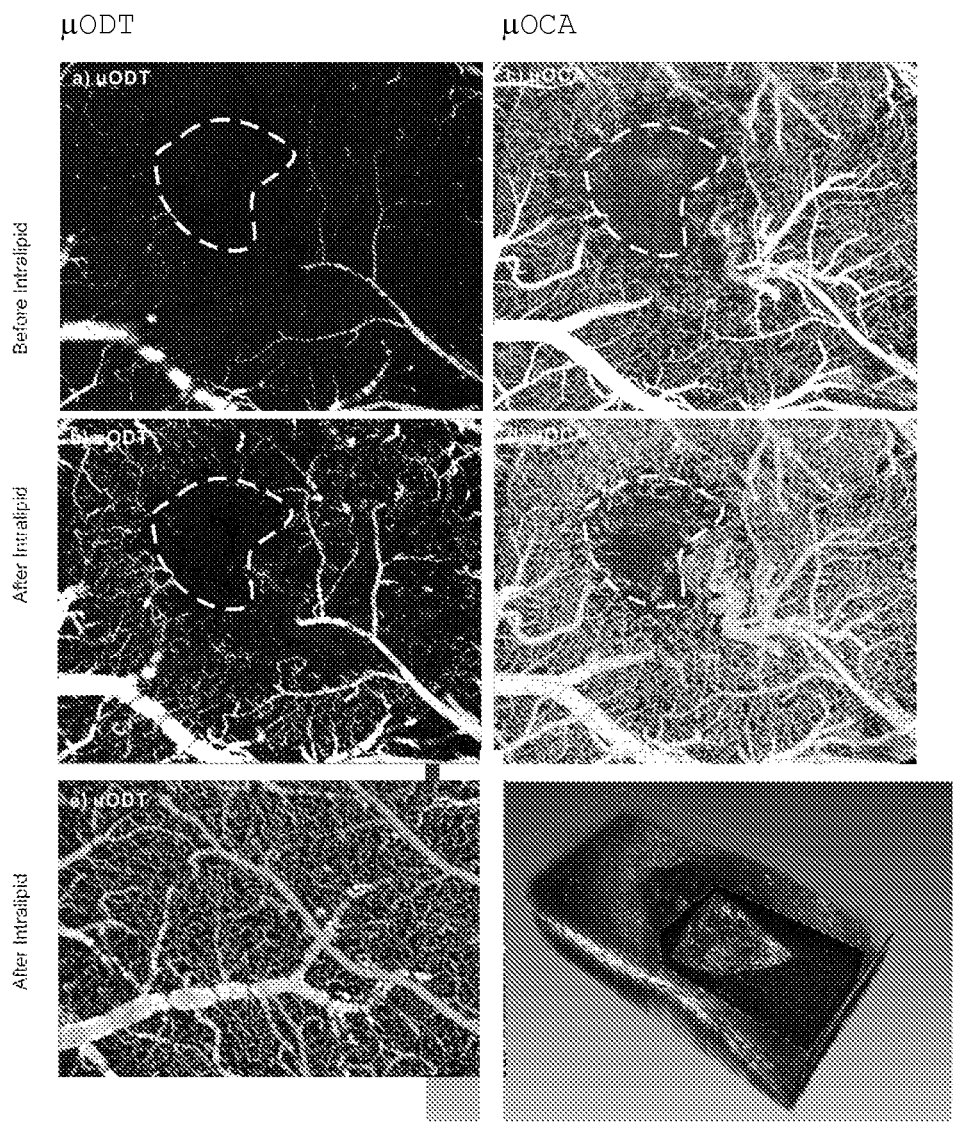
FIG. 7. μODT and μOCA images of a mouse subsurface brain tumor at 2 weeks after tropical implantation of cultured tumor cells. a, b): μODT images before and after intralipid injection; c), d): μOCA images before and after intralipid injection. Dotted circle: tumor boundary. e) μODT image (after intralipid injection) of the adjacent brain region for comparison. Because of substantially reduced CBF (consistent with tumor hypoxia) surrounding the tumor, the tumor vascular distribution which was unable to detect (a), was effectively enhanced and well delineated by intralipid injection. Interesting, angiography (μOCA) was unable to detect vasculatural difference of the surrounding tumor supply network (almost as dense as in normal regions).

FIG. 7 shows the study of tumor microenvironment in mouse brain at week 3 after brain tumor implantation. Depletion of blood flow within the tumor (tumor margin provided by μOCA as shown by yellow dashed circle) is clearly shown by μOCA (microangiography, see panes c & d). However, due to significantly reduced blood flow rate surrounding the tumor, μODT without intralipid (panel a) was unable to detect these slow/minute flows. However, the tumor margin in μODT image was recovered after intralipid injection (panel b). Importantly, the low supply of blood flow in the immediate adjacent area of the tumor as part of tumor hypoxia cannot be differentiated by μOCA; instead, it is clearly seen by μODT by a simple comparison of low capillary flow rate compared with normal brain region (panel e) away from the tumor, e.g., 65% lower. This result suggests that quantitative μODT with intralipid enhancement is more suitable for quantifying tumor microenvironment than angiography (μOCA), such as monitoring tumor therapeutic effect/efficacy.

Example 7. Additional Solutions

Additional solutions containing lipids or microlipids are used to image blood vessels or blood flow in blood vessels. Additional TPN or PN solutions containing lipids or microlipids, which are high scattering microparticles, are used as contrast agents for enhancing microcirculatory blood flow and imaging capillary blood flow. The solutions behave analogously to intralipid.

DISCUSSION

Despite a number of methods having been reported attempting to enhance Doppler flow imaging, the detection of microcirculatory blood flows remains a major technological challenge. This challenge is due to the angle effect (cos θ→0, when θ→90° and inherent phase noises induced by biological tissue micromotion during in vivo imaging. A major factor confounding the challenge lies in the fact that RBCs flowing through a capillary do not form laminal flows, but rather discrete flows.

It was found that in a φ5.6 μm capillary, the erythrocyte flux, mean $v_{RBC}$ and hematocrit of blood flow were −19/s, 0.72±0.15 mm/s and 7.1%. These results imply that in addition to the angle effect, the low RBC hematocrit in a capillary is a critical reason that leads to the underestimation of blood flow rate by LDF. This is because $v_{RBC}$ is derived from the total phase shift produced by the motion of RBCs whereas in less than 10% (e.g., 7.01%) of the time (latency) RBCs are actually counted and averaged over the entire time (e.g., >90% latency). Therefore, the blood flow in capillary vessels is substantially underestimated, which explains why a flow sensitivity as low as 10 μm/s is needed to measure capillary blood flow with a flow rate $v_{RBC}$ of 0.1-1 mm/s.

The use of intralipid as a contrast agent alleviates the aforementioned drawbacks of LDF. Intralipid is a composition of tiny lipids (around φ0.5 um) dispersed in aqueous solution. Since small scatterers such as the microlipids contained in the intralipid favor backscattering compared to the forward scattering of large RBCs (around φ07 um), they produce higher OCT signal than RBCs. Also, because of the small size of the intralipid, they tend to fill in the large latency (FIG. 6) between flowing RBCs to produce continuous Doppler shifts in a capillary vessel. These properties substantially enhance the ODT image of the microcirculatory network.

A comparison between the μOCA/μODT images (FIG. 1) showed significant image enhancement when intralipid (20%) was injected into the mouse prior to analysis. With iv injection of ~0.15 mL intralipid-20 into a 35 g mouse, a 300% image enhancement was achieved. This allowed for affirmative detection of the microcirculatory network. The upper panels in FIG. 1 show angiographic images and the lower panels show the corresponding Doppler flow images. μOCA is based on detection of the resultant intensity fluctuation whereas μODT is based on detection of directional Doppler flow. In our previous study (Ren et al. Optic Letter 2012), experimental results based on flow phantom and animal studies were obtained. It was found that that because of offset by Brownian motion of scattering particles including red blood cells, μOCA detects both directional and nondirectional flows (the latter is mostly caused by Brownian motion). Therefore, μOCA is more sensitive and is more suitable for detection of vasculature (blood vessel architecture). In parallel, μODT is more suitable for detecting directional or net flow, which is more sensitive for and more suitable for assessing flow, which is particularly relevant for studies of tissue physiology or of brain function.

Injection of saline (middle column, FIG. 1) showed no detectable difference with the baseline; whereas injection of intralipid substantially enhances the images of capillary beds. This renders intralipid a highly effective contrast agent to enhance blood flow imaging.

Since intralipid is clinically approved, it can be easily adopted for clinical applications. The present invention has significant impact on a wide variety of preclinical and clinical applications for the imaging assessment of the microvascular systems/networks. Applications include, but are not limited to, brain imaging, pharmacological imaging of brain physiology and function, cancer microenvironment (tumor angiogenesis) and therapy wound healing. Each of these applications requires enhanced imaging of microcirculation.

In particular, the method described herein is particularly useful for enhancing microcirculatory blood flow imaging in capillaries or in small vessels (i.e., arterioles and venules). Since in the brain most of the diffusion of oxygen and glucose occurs in the capillaries (which have small diameters), an increase in sensitivity is enormously valuable. The blood flow in the blood vessels of very small diameter, such as capillaries, is minimal and therefore difficult or impossible to detect with intralipid injection. The difficulty for imaging capillary blood flow is due to the long idle time between red blood cells passing thru a capillary (Ren et al. Appl. Phys. Lett. 2012) Intralipids fill the gap between two red blood cells, thereby overcoming this problem.

The method of applying intralipid is also extended to other types of scattering nutrition that are clinically used by intravenous injection or infusion.

REFERENCES

Chen, Z. et al. (1998) Photochemistry and Photobiology, Vol. 67, 1-7.
Chen, Z. et al. (1999) IEEE Journal of Selected Topics in Quantum Electronics, Vol. 5, No. 4, 1134-1142.
Draijer, M. et al. (2009) Review of laser speckle contrast techniques for visualizing tissue pattern, Lasers Med Sci, 24, 639-651.
Dunn, A. K. (2012) Laser speckle contrast imaging of cerebral blood flow, Annals of Biomedical Engineering, Vol. 20, No. 2, 367-377.
Hugang Ren, Congwu Du, Kicheon Park, Nora D. Volkow, and Yingtian Pan (2012) Quantitative imaging of red blood cell velocity invivo using optical coherence Doppler tomography. Appl. Phys. Lett. 100, 233702.
Hugang Ren, Congwu Du, and Yingtian Pan (2012) Cerebral blood flow imaged with ultrahigh-resolution optical coherence angiography and Doppler tomography. Optics Letters, 37 (8), 1388-1390.
Manavi, M. V. (2010) Lipid Infusion as a treatment for local anesthetic toxicity: a literature review. AANA J. 78, 1, 69-78.
Mirallo, J. M. et al. (2010) State of the art review: Intravenous fat emulsions: Current applications, safety profile, and clinical implications. Ann Pharmacother. 44, 4, 688-700.
Ren, H., C Du, Z Yuan, K Park, N D Volkow and Y Pan, (2012) Cocaine-induced cortical microischemia in the rodent brain: clinical implications, Molecular Psychiatry, 10, 1017-1025.
Rosenblatt M A, Abel M, Fischer G W, Itzkovich C J, Eisenkraft J B. (2006) Successful Use of a 20% Lipid Emulsion to Resuscitate a Patient after a Presumed Bupivacaine-related Cardiac Arrest. Anesthesiology, 105, 217-218.
Vakoc, B. J. et al. (2009) Three-dimensional microscopy of the tumor microenvironment in vivo using optical frequency domain imaging, Nature Medicine, Vol. 15 (10), 1219-1223.
Wang R K, Jacques S L, Ma Z, Hurst S, Hanson S R, Gruber A. (2007) Three dimensional optical angiography. Optics Express, Vol 15, No 7, 4083-4097.
Yuan Z, Luo Z, Volkow N, Pan Y, Du C. (2011) Imaging separation of neuronal from vascular effects of cocaine on rat cortical brain in vivo. Vol 54, No 2, 1130-1139.

What is claimed is:

1. A method of distinguishing between different types of animal microvasculature in an animal, comprising:
   (i) injecting a lipid solution into a bloodstream of the animal;
   (ii) performing a plurality of imaging scans of microvasculature of the animal using Optical Doppler Tomography (ODT);
   (iii) determining a Doppler shift produced by the lipid solution based on the imaging scans;
   (iv) calculating a blood flow velocity and a blood flow direction in the microvasculature based on the Doppler shift; and
   (v) distinguishing between different types of the animal microvasculature based on the blood flow velocity and the blood flow direction.

2. The method of claim 1, wherein the lipid solution includes at least one of a fat emulsion, a total parenteral nutrition solution, a parental nutrition solution, or a total peripheral nutrition solution.

3. The method of claim 2, wherein the at least one of the fat emulsion, the total parenteral nutrition solution, the parental nutrition solution, or the total peripheral nutrition solution is a contrast agent.

4. The method of claim 2, further comprising generating a three-dimensional image of the microvasculature.

5. The method of claim 2, wherein the fat emulsion has a fat concentration of at least one of 10%, 20% or 30%.

6. The method of claim 1, wherein the lipid solution is a contrast agent.

7. The method of claim 1, wherein the animal is a mammal.

8. The method of claim 7, wherein the mammal is a human.

9. The method of claim 1, wherein the distinguishing between different types of animal microvasculature includes distinguishing a tumor microvasculature from a non-tumor microvasculature.

10. The method of claim 9, wherein the tumor is a glioblastoma multiforme.

11. The method of claim 1, wherein the Doppler shift is a continuous Doppler shift.

12. The method of claim 1, further comprising:
    determining a backscattering of a light produced by the lipid solution based on the imaging scans; and
    calculating the blood flow velocity and the blood flow direction in capillaries based on the Doppler shift and the backscattering of the light.

13. A method of distinguishing between different types of animal microvasculature comprising:
    (i) injecting a lipid solution into a bloodstream of an animal;
    (ii) performing a plurality of imaging scans of microvasculature of the animal using Optical Doppler Tomography (ODT);
    (iii) determining a Doppler shift produced by the lipid solution based on the imaging scans;
    (iv) calculating a blood flow velocity and a blood flow direction in the microvasculature based on the Doppler shift;
    (v) quantitatively determining a blood flow velocity change following the lipid solution injection; and
    (vi) distinguishing between different types of the animal microvasculature based on the blood flow velocity, the blood flow direction, and the blood flow velocity change.

14. The method of claim 13, wherein the lipid solution includes at least one of a fat emulsion, a total parenteral nutrition solution, a parental nutrition solution, or a total peripheral nutrition solution.

15. The method claim 13, wherein the Doppler shift is a continuous Doppler shift.

16. The method of claim 13, further comprising:
    determining a backscattering of a light produced by the lipid solution based on the imaging scans; and
    calculating the blood flow velocity and the blood flow direction in capillaries based on the Doppler shift and the backscattering of the light.

17. An Optical Doppler Tomography (ODT) method for distinguishing between different types of animal vasculature comprising:
    (i) injecting a lipid solution into a bloodstream of an animal so that the blood stream carries the lipid solution to a specific site;
    (ii) applying a laser beam to the specific site so as to generate a Doppler frequency shift of the laser caused by the lipid solution flowing through capillaries at the specific site;
    (iii) generating a three-dimensional tomographic image of the capillaries at the specific site on the basis of the Doppler frequency shift of the laser;
    (iv) calculating a blood flow velocity and a blood flow direction in the capillaries at the specific site on the basis of the Doppler frequency shift of the laser; and
    (v) distinguishing between different types of the animal microvasculature based on the blood flow velocity and the blood flow direction.

18. The method of claim 17, wherein the lipid solution includes at least one of a fat emulsion, a total parenteral nutrition solution, a parental nutrition solution, or a total peripheral nutrition solution.

19. The method of claim 17, further comprising imaging the capillaries or the blood flow in the capillaries three or more times following the injection of the lipid solution.

20. The method of claim 19, wherein the imaging the capillaries or the blood flow in the capillaries is performed about 1 hour following the injection of the lipid solution.

21. The method of claim 19, wherein the imaging the capillaries or the blood flow in the capillaries is performed about 3 hours following the injection of the lipid solution.

22. The method of claim 19, wherein the imaging the capillaries or the blood flow in the capillaries is performed about 6 hours following the injection of the lipid solution.

23. The method claim 17, wherein the Doppler shift is a continuous Doppler shift.

24. The method of claim 17, further comprising:
    determining a backscattering of a light produced by the lipid solution based on the three-dimensional tomographic image; and
    calculating the blood flow velocity and the blood flow direction in the capillaries based on the Doppler frequency shift and the backscattering of the light.

25. A method of distinguishing between different types of animal microvasculature in an animal, comprising:
    (i) injecting a lipid solution into a bloodstream of the animal;
    (ii) imaging microvasculature of the animal using an Optical Doppler Tomography (ODT) system having an axial resolution of about 1.8 μm and a transverse resolution of about 3 μm;
    (iii) calculating a blood flow velocity and a blood flow direction in the microvasculature; and (iv) distinguishing between different types of the animal microvasculature based on the blood flow velocity and the blood flow direction.

\* \* \* \* \*